United States Patent [19]
Tom et al.

[11] Patent Number: 6,030,591
[45] Date of Patent: *Feb. 29, 2000

[54] PROCESS FOR REMOVING AND RECOVERING HALOCARBONS FROM EFFLUENT PROCESS STREAMS

[75] Inventors: Glenn M. Tom, New Milford, Conn.; H. Eric Fisher, Boulder, Colo.; W. Karl Olander, Indian Shore, Fla.

[73] Assignee: ATMI Ecosys Corporation, San Jose, Calif.

[ * ] Notice: This patent is subject to a terminal disclaimer.

[21] Appl. No.: 09/002,519

[22] Filed: Jan. 2, 1998

Related U.S. Application Data

[63] Continuation of application No. 08/474,517, Jun. 7, 1995, abandoned, which is a continuation-in-part of application No. 08/395,162, Feb. 27, 1995, Pat. No. 5,622,682, which is a continuation of application No. 08/224,294, Apr. 6, 1994, abandoned.

[51] Int. Cl.⁷ .................................................. C01B 7/00
[52] U.S. Cl. .................. 423/240 S; 423/210; 423/219; 423/225; 423/230; 423/234; 423/235; 423/239.1; 423/240 R; 423/241; 423/246; 423/247
[58] Field of Search ................ 423/240 R, 240 S, 423/210, 219, 225, 230, 234, 235, 239.1, 241, 246, 247

[56] References Cited

U.S. PATENT DOCUMENTS

| | | | |
|---|---|---|---|
| 4,070,164 | 1/1978 | Miwa et al. | 55/26 |
| 4,581,209 | 4/1986 | Oswald et al. | 423/234 |
| 4,604,270 | 8/1986 | Tom | 423/210 |
| 4,645,516 | 2/1987 | Doshi | 55/16 |
| 4,933,158 | 6/1990 | Aritsuka et al. | 423/210 |
| 4,964,137 | 10/1990 | Aramaki et al. | 372/59 |
| 5,091,358 | 2/1992 | Birbara et al. | 423/230 |
| 5,137,550 | 8/1992 | Hegarty et al. | 423/220 |
| 5,322,674 | 6/1994 | Mori | 423/240 S |
| 5,502,969 | 4/1996 | Jin et al. | 62/11 |
| 5,622,682 | 4/1997 | Tom | 423/240 S |
| 5,779,998 | 7/1998 | Tom | 423/240 S |

FOREIGN PATENT DOCUMENTS

| | | | |
|---|---|---|---|
| 256692 | 5/1988 | Germany | 95/142 |
| 3-135410 | 6/1991 | Japan . | |
| 4-118024 | 4/1992 | Japan . | |
| 2020566 | 11/1979 | United Kingdom | 95/142 |
| 88-01534 | 3/1988 | WIPO | 95/142 |

OTHER PUBLICATIONS

*Structural Chemistry of Inorganic Compounds*, Huckel, pp. 663–665 London, 1951 (no month).
*Chemical Principals*, 4th ed., Masterton and Slowinski, pp. 221–222, 1977 (no month).
*Inorganic Polymers*, Hunter, pp. 9–10, 1963 (no month).
"The Adsorption Of Vapours By Activated And Heat–Treated Carbons—Part I . . ." R. H. Bradley, *Carbon*, 29(7), 893–897 (1991).
"Adsorption Rate Coefficients For Gases And Vapors On Activated Carbons" Wood, G. O., Stampfer, J. F. *Carbon*, 31(1), 195–200 (1993).
SOLTRAP Product Literature, American Morikawa Industries Corp., Feb. 3, 1994.

*Primary Examiner*—Steven P. Griffin
*Assistant Examiner*—Stuart L. Hendrickson
*Attorney, Agent, or Firm*—Steven J. Hultquist; Thomas C. Mavrakakis; Oliver A.M. Zitzmann

[57] ABSTRACT

A process for recovery of fluorocompound gas from an effluent gas stream containing the fluorocompound gas and other gas components, in which at least one of the other gas components is removed, e.g., by oxidation or contacting of the effluent stream with a dry material such as an adsorbent or scrubber medium, to yield a first effluent gas mixture containing the fluorocompound gas. The fluorocompound gas is removed from the first effluent gas mixture and recovered as a concentrated fluorocompound gas, by a process such as cryogenic processing, membrane separation, and/or adsorption.

16 Claims, 3 Drawing Sheets

PROCESS FOR REMOVING AND RECOVERING HALOCARBONS FROM EFFLUENT PROCESS STREAMS

This is a continuation of U.S. patent application Ser. No. 08/474,517 filed Jun. 7, 1995 in the names of Glenn M. Tom, H. Eric Fisher and W. Karl Olander for "PROCESS FOR REMOVING AND RECOVERING HALOCARBONS FROM EFFLUENT PROCESS STREAMS," now abandoned, which is a continuation-in-part of U.S. patent application Ser. No. 08/395,162 filed Feb. 27, 1995 in the name of Glenn M. Tom for "METHOD FOR CONCENTRATION AND RECOVERY OF HALOCARBONS FROM EFFLUENT GAS STREAMS," issued Apr. 22, 1997 as U.S. Pat. No. 5,622,682, which in turn is a continuation of U.S. patent application Ser. No. 08/224,294, filed Apr. 6, 1994 in the names of Glenn M. Tom and H. Eric Fisher for "PROCESS FOR REMOVING AND RECOVERING HALOCARBONS FROM EFFLUENT PROCESS STREAMS," now abandoned.

BACKGROUND OF THE INVENTION

1. Field of the Invention

This invention relates to a method and apparatus for concentration and recovery of halocarbons from process effluent gas streams. The present invention further relates to a process of removing by-products and impurities from halocarbon-containing waste streams to enhance such concentration and recovery process.

2. Description of the Related Art

Fluorinated and chlorinated compounds are used in semiconductor etch, chemical vapor deposition ("CVD"), and process tool cleaning processes. Examples of compounds which are widely used in such processes include perfluorocarbons ("PFCs"), fluorinated hydrocarbons, and chlorofluorocarbons as well as sulfur hexafluoride and nitrogen trifluoride, all of which will be collectively referred to herein as "halocarbon." Specific examples include $C_2F_6$, $CF_4$, $CHF_3$ and $SF_6$. These compounds are suspected of causing global warming by what has come to be known as a "greenhouse" effect. While long-term effects are unknown, current data suggest that compounds of this type are accumulating in increasing concentrations in the upper atmosphere, and that they can persist there for thousands of years. Manufacturers of many of these compounds, especially the perfluorocarbons are establishing policies that require customers to ensure that a high percentage of the PFCs are recycled or prevented form reaching the atmosphere. The U.S. Environmental Protection agency is requiring that PFC emission levels return to 1990 levels by the year 2000.

Incineration (combustion) has been shown to be an effective means of destroying halocarbons including PFCs. However, incineration requires considerable capital investment. In addition, because of the stability of PFCs, they must be heated to over 1000° C. before oxidation occurs. The reaction that takes place:

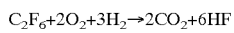

$$C_2F_6 + 2O_2 + 3H_2 \rightarrow 2CO_2 + 6HF$$

produces toxic and corrosive hydrogen fluoride, which must then be neutralized. Typically, a wet scrubber would be used to neutralize the hydrogen fluoride, adding to the overall cost and complexity, and generating large volumes of aqueous waste whose disposal may be inconvenient. Also, burning processes that involve hydrogen raise safety concerns. If the halocarbon is present in the effluent stream in a dilute concentration, incineration is especially cost-ineffective. In general, in the effluent streams from semiconductor etch reactors, the halocarbon species are expected to be present in concentrations of only a few percent, e.g., 0.1–5%.

Halocarbon recovery and recycling is an approach potentially providing advantages to the environment as well as providing a simpler apparatus and methodology for keeping halocarbon emissions to a minimum. Recovery and recycling are relatively simple for the liquid halocarbons, which can be trapped by refrigeration units. For the gaseous halocarbons, this approach may be too energy-intensive. However, it has been found that because of their chemical inertness, the perfluorocarbons, sulfur hexafluoride ($SF_6$), and the Freons ($CF_4$, $C_2F_6$, and $CHF_3$) that are used in the semiconductor industry are well-suited to recovery by adsorptive processes.

It is known that halocarbons may be adsorbed by various sorbent materials, including porous carbons, zeolites, silicas and aluminas. Wood and Stampfer (Carbon 31, pp. 195–200, 1993) studied adsorption for fifteen fluorocarbons on beds of activated carbon such as are used for removing gases and vapors from air. Their data may be used to predict the performance of a sorbent bed for any of these fluorocarbons after the bed has been characterized for one of the compounds. Packed beds of such activated carbons are used in applications ranging from air sampling tubes, respirator cartridges, to large industrial effluent filters, to adsorb halocarbons. Beds of porous adsorbent materials have been reported to be useful for the separation and recovery of volatile fluorocarbons.

Izumi et al. (Japanese Patent Application 03/135,410, Jun. 10, 1991) describes the adsorption of volatile substances including halocarbons on various high surface area adsorbents, such as gamma-alumina, activated carbon, high silica zeolite, silica superfine particles, or silica gel, at an adsorption pressure of 1–2 atmospheres, followed by desorption at a reduced pressure, preferably about 1/10 of the pressure at which the adsorption step took place. However, this process is better adapted to halocarbons which are liquids at room temperature, since the system provides liquefied recovered halocarbon. Water is removed using an adsorbent such as potassium Amberlite (K-A) or sodium Amberlite (Na-A) type zeolite, which adsorbs water but does not adsorb organic substances, from the concentrated halocarbon after it is desorbed from the sorbent bed.

Recovery of fluorocarbons from semiconductor etch, CVD, and cleaning process effluents is, moreover, complicated by the presence of other toxic or corrosive components in the gaseous waste (effluent) stream. Typically, the other waste gases can include corrosive species such as HF, or in for example, tungsten etch processes, tunsten oxyfluoride ($WOF_4$) and tunsten hexafluoride ($WF_6$). Other species present can include $SiF_4$, $F_2$, or $COF_2$. Plasma processes may generate a large variety of by-product species because of chemical reactions such as rearrangement or scrambling that can occur in the high energy plasma. The table below presents a non-exhaustive list of possible species in the exhaust of a reactor in which $C_2F_6$ is used in a plasma process for cleaning steps in silicon processing. Many of these materials are hazardous to personnel because of their corrosivity and toxicity.

In Table I below are listed a number of typical species present in the exhaust stream of a CVD cleaning process.

TABLE I

CVD CHAMBER CLEAN
LIST OF POSSIBLE SPECIES IN EXHAUST STREAM

| Name | Formula | MW | Vapor Pressure Kpa | T °C. | Boiling T °C. | Critical T °C. |
|---|---|---|---|---|---|---|
| Carbonyl fluoride | $COF_2$ | 66.007 | 5,620 | 21.1 | −84.6 | 22.8 |
| Carbon dioxide | $CO_2$ | 44.011 | | | | 31.1 |
| Carbon monoxide | CO | 28.010 | | | −191.5 | −140.2 |
| Carbon tetrafluoride | $CF_4$ | 88.005 | 1.33 | −169 | −128.0 | −45.6 |
| Decafluoro-butane | $C_4F_{10}$ | 238.028 | 330 | 31.7 | −2.0 | 113.2 |
| 1,1-Difluoro-ethylene | $H_2C_2F_2$ | 64.035 | 3,571.5 | 21.1 | −85.7 | 29.7 |
| Dioxygen difluoride | $F_2O_2$ | 70.0 | 1.33 | −120 | | |
| Fluorine | $F_2$ | 37.997 | | | −188.1 | −128.8 |
| Hexafluoro disilane | $Si_2F_6$ | 170.162 | 0.0133 | −96 | | |
| Hexafluoro-ethane | $C_2F_6$ | 138.012 | 3,070 | 21.1 | −78.2 | 19.7 |
| Hexafluoro-propylene | $C_3F_6$ | 150.023 | 687.4 | 21.1 | | 94.0 |
| Hydrogen fluoride | HF | 20.006 | 103 | 20 | 19.5 | 188.0 |
| Octafluoro-cyclobutane | $C_4F_8$ | 200.031 | 274 | 21.1 | −5.8 | 115.3 |
| Octafluoro-propane | $C_3F_8$ | 188.021 | | | | |
| Oxygen difluoride | $F_2O$ | 53.996 | 0.0133 | −205 | −144.9 | −58.0 |
| Perfluoro-isobutylene | $C_4F_8$ | 200.031 | | | | |
| Silicon tetrafluoride | $SiF_4$ | 104.08 | 0.0133 | −155 | | −14.2 |
| Tetrafluoro-ethylene | $C_2F_4$ | 100.016 | 3,040 | 21.1 | −76.3 | 33.3 |

The presence of these and other contaminants in process effluents can cause serious problems in adsorption-based recovery/recycle systems. The void space of the adsorbent can be filled with reaction products. This fouling of the adsorbent bed can destroy its ability to be regenerated, which seriously degrades the economics of recovery/recycle. In addition, the feed stream for a recycling process needs to be as clean as possible to make recycle economically attractive. Allowing these corrosive contaminants to remain in the gaseous effluent stream can lead to corrosion of ductwork and valves, and eventually to system failure. And finally, environmental regulations prohibit venting significant quantities of HF or other corrosive gases to the atmosphere.

The presence of these other contaminants can also produce problems in recovery systems using cryogenic recovery systems. Moreover, the presence of water in effluent streams will foul recovery systems using adsorbents as well as cryogenic recovery systems.

In addition to the by-products generated from halocarbon starting materials in the wafer processing step, other hazardous components may be present in the effluent gas stream along with the halocarbon. Corrosive, reactive, flammable and/or poisonous gases may be used in processing steps along with the halocarbon or the effluent from which becomes mixed with the halocarbon-containing effluent gas stream. Examples include arsine (toxic) used in metallorganic chemical vapor deposition, boron trichloride (corrosive) used in etch or cleaning steps and silane (extremely flammable) used in silicide deposition.

Hence, providing a relatively clean, dry, and inert incoming stream to a concentration and recovery unit for halocarbons will help to maximize its capacity and efficiency as well as avoid hazards to personnel and equipment.

SUMMARY OF THE INVENTION

Accordingly, it is an object of the present invention to provide a method and apparatus for concentration and recovery of volatile halogenated compounds such as perfluorocarbons, fluorinated hydrocarbons, chlorofluorocarbons, and $SF_6$, all generically referred to herein as halocarbons. The method and apparatus are suitable for use with process effluents that may be contaminated with any number of by-products, including corrosive ones and is able to provide a clean, concentrated stream of recovered halogenated compound, suitable for recycle.

In one aspect, the present invention provides for a process for recovery of halocarbons from effluent gas streams. The gas streams comprise a carrier gas, halocarbons, byproducts generated from a process employing the halocarbons and producing by-products, and optionally contaminating process gases. The process comprises the steps of contacting the gas stream with at least one scrubber to remove said by-products from the gas stream, thereby yielding a first effluent gas mixture containing the halocarbon and being substantially free of the by-product. The first effluent gas mixture is subjected to a process for removing the halocarbon from said effluent gas mixture and concentrating same for subsequent recovery of said halocarbon.

For purposes of the present invention, substantially free of by-product is intended to mean that the amount of by-product in the effluent stream is negligible enough not to interfere with or influence the halocarbon recovery process, not to contaminate and corrode apparatus or system parts and not to cause a potential health hazard to personnel.

For purposes of the present invention, scrubber and scrubber composition is intended to mean chemical compositions or physical processes that react with and deactivate by-products of the process using halocarbons. Carrier gas is intended to mean any gas or mixture thereof originating from a process using halocarbons.

Other objects advantages, aspects and features of the invention will be more fully apparent from the ensuing disclosure and claims.

DETAILED DESCRIPTION OF THE INVENTION, AND PREFERRED EMBODIMENTS THEREOF

Figure 1:
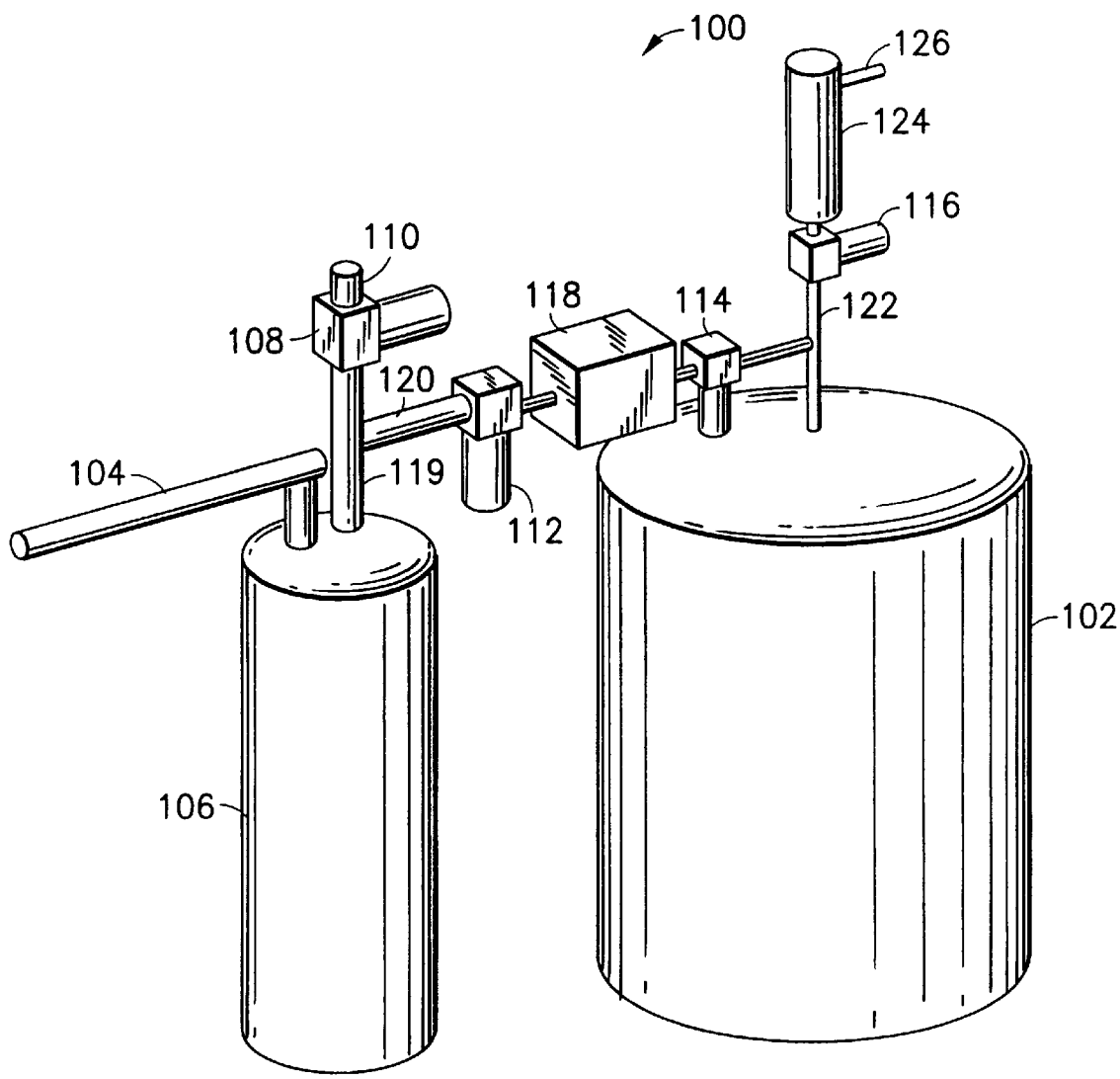
FIG. 1 shows a schematic of a simple system for recovery of halocarbons from effluent gas streams, employing one adsorbent bed, which is cycled between a high pressure adsorption step and a low pressure desorption step.

In a preferred embodiment the present invention is directed to a process for recovery of halocarbons from effluent gas streams. The gas streams are effluent streams from processes employing the halocarbons and generating by-products and comprise a carrier gas, halocarbons, byproducts, and optionally contaminating process gases. The process comprises, inter alia, contacting the gas stream with at least one scrubber to remove the by-products from the gas stream, thereby yielding a first effluent gas mixture containing the halocarbon and being substantially free of the by-product.

The first effluent gas mixture is subjected to a process for removing the halocarbon from the effluent gas mixture and concentrating same for subsequent recovery of said halocarbon.

In a preferred embodiment, the present invention comprises a process for recovering a compound selected from the group consisting of perfluoroethene, perfluoroethane, trifluoromethane, carbon tetrafluoride, sulfur hexafluoride and mixtures thereof. The concentration of halocarbon in the gas mixture may be as low as from 0.01% to 5% by weight, based on the total weight of the gas mixture. The concentration of by-product in said effluent gas mixture is from 0.01% to 5% by weight, based on the total weight of the gas mixture.

In the present process, the choice of an appropriate scrubber or combination of scrubbers should preferably be based on the by-products generated. Examples of appropriate scrubbers for use in the present invention, include but are not limited to wet scrubbers, dry scrubbers such as metallo-oxomeric ablative scrubbers, catalytic enhanced oxidizers, flame oxidizers, thernmal oxidizers and combinations thereof.

When the by-products to be removed include water soluble or water reactive species, removal of the by-products from the effluent gas stream may be accomplished by wet or water-based scrubbers. Examples of by-products that may be removed by wet scrubbers include, but are not limited to HCl, $SiH_2Cl_2$, $SiHCl_3$, $SiCl_4$, $NH_3$, BCl3, HF, TEOS, $BF_3$, $Cl_2$, $WF_6$, and HBr. Using wet scrubbing, an exhaust gas stream from a process using halocarbons may also be processed using aqueous solutions of relatively inexpensive basic reagents such as for example sodium hydroxide, lithium hydroxide, ammonium hydroxide, etc.

In situations wherein the gaseous effluent contains highly reactive compounds such as silane (which is not soluble in water but reacts readily with oxygen), a thermal oxidizer, an active flame oxidizer or dry scrubber is included.

Hence, when at least one by-product is a hydride, silane, oxynitride, silane/oxygen mixtures, silane/$NF_3$ mixtures, perfluoro compounds and combinations thereof, at least one scrubber may be an active flame oxidizer, as for example the oxidizer disclosed and claimed in U.S. Pat. No. 5,183,646, hereby incorporated by reference herein. Preferably, such active flame oxidizers are run at such temperature to avoid destroying the halocarbon content of the effluent stream.

Moreover, for an adsorption-based concentration and recovery system to operate economically, the water vapor generated by the wet scrubbers would then need to be removed from the scrubber effluent, or else the adsorption capacity of the sorbent bed would be largely consumed by water molecules which compete for the same adsorption sites. In addition, in most cases water would not desorb as readily as the halocarbon component from the adsorption bed. Therefore, water vapor contamination will, over time, seriously compromise the effectiveness of the concentration and recovery unit. Additionally, in recovery systems using cryogenic units, the water would freeze out of the stream, thereby seriously effecting the efficiency of the system.

Hence, the process according to the present invention may optionally include a drying step after at least one contacting step whereby water is removed from the effluent gas mixture. The drying step may be carried out using any known water removal system including water complexing metal oxides, gas blowers, a heat regenerable dryer, a molecular sieve, silica gel or cold trap dryer. Cold trap dryers are pseudo-cryogenic dryers whereby the gas mixture containing the water vapor flows over a cold surface and the water condenses out.

Dry scrubbing is therefore an alternative for providing a relatively clean gas stream for recovery and recycle of halocarbons, because it does not contribute appreciable water vapor to the effluent stream. In addition, dry scrubbers operate passively and therefore do not require much energy or complicated equipment design.

Dry scrubbers or metallo-oxomeric ablative scrubbers are preferably used when at least one by-product is a member of the group consisting of hydrides, and reactive acids gases such as carbonyl fluoride, dioxygen difluoride, fluorine, hexafluorodisilanc, hydrogen fluoride, oxygen difluoride, silicon tetrafluoride, and tungsten hexafluoride ($WF_6$).

With dry scrubbing, the flow characteristics and therefore the contact time of the gas with the scrubber may be adjusted by varying the porosity or particle size of the scrubber or selection of appropriate support material. In applications involving high flow rates, the scavenger may thereby be tailored for high kinetic efficiency; conversely under conditions of low flow, a highly loaded, high capacity support may be selected. To gain the advantages of both high efficiency and high capacity, scrubber beds may comprise more than one type of scrubber combination, in layered or mixed form.

A good effluent gas scrubber must not only remove hazardous gas components to low levels, preferably below their Threshold Limit Volume/Personal Exposure Limit (TLV/PEL) limits, but must also possess several other attributes. It must operate safely, with no risk of explosion or spillage. It should have high capacity for the hazardous components, so that it need not require an extremely large volume for scrubbing or frequent change-outs. It must have high kinetic efficiency for scrubbing, so that high flow rate effluent gas streams may be scrubbed. Scrubbers of a simple, passive design are preferred, since they are likely to be more economical. Finally, the scrubber should convert the hazardous components of the effluent gas stream to stable, environmentally acceptable species that may be disposed of safely and economically.

Typical dry scrubbers for use in the present invention, include, but are not limited to metal hydroxides and metal oxides such as for example, goethite, copper oxide, copper oxide/zinc oxide mixtures, copper sulfate, calcium oxide, lithium hydroxide and mixtures thereof U.S. Pat. Nos. 5,151,395, 4,743,435, 4,996,030, 5,024,823 and 4,535,072, the disclosures of which are hereby incorporated herein by reference disclose additional dry scrubbers for use in the invention. Metallo-oxomeric ablative scrubbers are described in U.S. Pat. No. 5,777,058 filed May 29, 1996 in the name of H. Eric Fisher for "METALLO-OXOMERIC SCRUBBER COMPOSITIONS, AND METHOD OF GAS PURIFICATION UTILIZING SAME," the disclosure of which is hereby incorporated herein by reference.

In a preferred embodiment of the present invention, the effluent gas stream is contacted with more than one scrubber, which may be the same or different and the contacting is done in series. Alternatively or additionally, the effluent gas stream may be contacted with more than one scrubber and contacting is done in a closed loop parallel for redundancy.

In a typical embodiment of the present invention, the process for removing the halocarbon and concentrating same may be comprised of contacting at least one time and under superatmospheric pressure, the first effluent gas mixture with an adsorbent which is selective for the halocarbon component of the first effluent gas mixture to adsorb said halocarbon component on the adsorbent and yield a second effluent gas substantially free of halocarbon, and recovering the adsorbed halocarbon by applying a vacuum and preferably heat as required, thereby desorbing same from the adsorbent. Alternatively, the process for removing the halocarbon may be comprised of subjecting at least one time, the first effluent gas mixture to a cryogenic recovery system to concentrate and recover said halocarbon.

In the present invention when the process for removing the halocarbon and concentrating same is carried out by a cryogenic recovery system, the effluent gas stream is contacted with vaporized liquid Nitrogen, thereby producing a liquified or solidified halocarbon condensate.

In the present invention process said first effluent gas mixture contacted with said adsorbent may be confined against a selective membrane allowing passage therethrough of non-halocarbon component(s), to concentrate the halocarbon components and allow discharge from the process of gas components other than halocarbons components. Selectively permeable membranes that are useful in this embodiment of the invention include cellulosics, polysulfones, and perfluorinated polymer membranes. Alternatively, or additionally, the discharged halocarbon may be compressed and flowed to a gas cylinder.

In one embodiment, the present invention employs a pressure swing adsorption (PSA) process to recover halocarbons from effluent gas streams in which they may be dilute, that is, present in concentrations of 0.1 to 5%. One objective of the invention is to achieve high recovery from a dilute stream, which is more difficult than the recovery of a gas at high purity from bulk streams. Application of thermodynamic principles to a potential PSA process shows that the theoretical maximum concentration increase is equal to the pressure ratio of the PSA times the inlet concentration for dilute components as follows:

$$\text{Conc.}_{out}\text{Max.} = \text{Concentration}_{in} \times (\text{Pressure}_{ads}/\text{Pressure}_{desorp});$$

where $\text{Conc.}_{out}\text{Max.}$ is the maximum outlet concentration from the PSA system for a dilute feed component; $\text{Pressure}_{ads}$ is the inlet pressure to the adsorption bed at pressure; and $\text{Pressure}_{desorb}$ is the lower desorption pressure during system operation.

This concentration increase limit however applies for a single pressure swing sequence and is obviously limited to a maximum value of 100%. The concentration increase can potentially be enhanced by a repeat of the cycle with the partially concentrated gas as the feed. Such a scheme may for example be used for high recovery of fluorocarbons (and $SF_6$) from gases containing oxygen and nitrogen. Sorption beds for a PSA process can range from several inches in diameter to several feet in diameter and can be simple in design. Complexity is focused in the valving for operation and any extra compression and decompression steps. Automatic operation is preferred because of the rapid cycles utilized. Established PSA processes cycle from every few seconds up to perhaps every 10 minutes. The key is using an adsorbent material which is selective for the halogen-containing materials while it is non-selective or non-sorptive for the diluents (nitrogen and oxygen). High surface area adsorbents such as activated carbon, molecular sieves, aluminas, silica gel, and macroreticulate organic polymers such as Amberlite (Rohm & Haas) meet this requirement. Activated carbon is preferred.

Hence, in the present invention the recovery may be carried out by providing at least two adsorbent beds, each of said adsorbent beds having inlet and outlet ends, respectively, and joined at inlet and outlet ends thereof to gas feed and gas discharge manifolds, respectively, wherein said first effluent gas mixture is introduced to one of said adsorbent beds from said gas feed manifold at superatmospheric pressure to effect adsorption of halocarbon on the bed, and contemporaneously another of said adsorbent beds is depressurized following adsorption of halocarbon thereon, to desorb the adsorbed halocarbon and to discharge same from the bed through said gas discharge manifolds at lower-than-first superatmospheric pressure, and wherein such steps are alternatively and repetitively carried out in respective adsorbent beds.

In order to make recycling economically attractive, the concentration and recovery unit must be able to provide a concentrated stream of halocarbons for further purification or processing. Concentration of the recovered halocarbon gas or vapor may be accomplished by compression or liquefaction.

FIG. 1 shows a simple concentration and recovery process system 100 according to one embodiment of the present invention using one sorbent bed 102. The process effluent stream is flowed by conduit 104 from its source such as a semiconductor manufacturing plant (not shown) to scrubber vessel 106 for contacting with a scavenger in a scrubber bed of same in the vessel. In the scrubber vessel 106, the process effluent stream is treated in the scrubber bed by a scavenger to remove hazardous and solid-forming materials. On a signal (from the use or process monitoring means not shown in FIG. 1) that halocarbon is in the effluent stream, isolation valve 108 (joined to vent line 110) closes and isolation valves 112, 114, and 116 open. A compression pump 118 in conduit line 120 sweeps the remaining non-hazardous gas mixture through lines 119 and 120 into the vessel 102 which is filled with a suitable adsorbent for halocarbons such as activated carbon. When the pulse of halocarbon-containing effluent has passed, isolation valves 108 and 112 close. The halocarbons adsorb onto the carbon bed at a loading of up to 10% at 1 atmosphere. Nitrogen and possibly oxygen (which are not adsorbed by the adsorbent in vessel 102) flow through line 122 and isolation valve 116 therein to selective membrane device 124 equipped with diffused gas outlet conduit 126. The selective membrane device 124 comprises a selectively permeable membrane so that the non-adsorbed gases will diffuse out of the selective membrane and be discharged from the system in line 126. After the gas pressure in vessel 102 is reduced to a selected pressure level, isolation valve 116 will close. This adsorption process and concentration cycle can be repeated many times. The carbon bed can be used many times after desorption of the adsorbed halocarbon.

Figure 2:
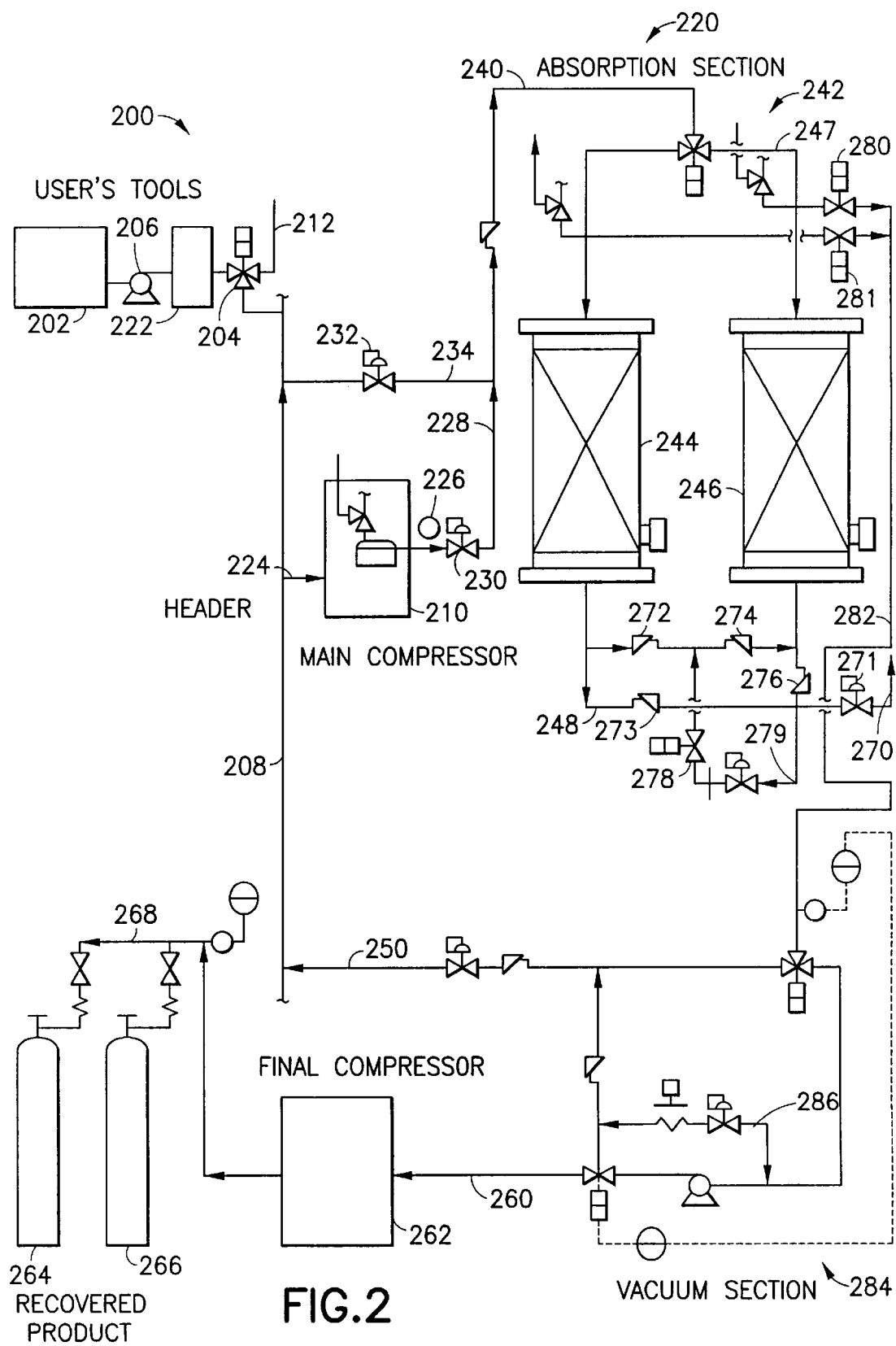
FIG. 2 shows a process flow schematic for the scrubbing, concentration, and recovery steps that comprise one embodiment of the method of the present invention, employing two canisters of adsorbent which are pressure-cycled alternatively to provide continuous service.

FIG. 2 shows a block flow diagram for a process system 200 according to another embodiment of the invention, for processing halocarbon-containing gas mixtures from a semiconductor wafer fabrication facility including wafer fabrication tool 202. A brief description of each block follows.

Collection of the halocarbon gases is accomplished at the wafer fabrication tool 202 ahead of any scrubbers. A tie-in is made with a three-way valve 204 which routes gases after the tool's vacuum pump exhaust, from vacuum pump 206 through scrubber 222 to other existing treatment equipment (not shown) or simple discharge via discharge line 212 or to the recovery system 220. Each separate source of halocarbon from a multisource (multitool) process system suitably has a tie-in similar to that shown with a three-way valve for control of the collected gas flow. Such a system allows operation when there are no halocarbons at the fab tool, as the fab system conventionally operates, by routing the gas discharge through the discharge line 212. During tool operation with a halocarbon flow, the three-way valve 204 routes the stream (after the fab tool vacuum pump 206) from the scrubber vessel 222 into a collection header 208.

The collection header 208 is maintained at slight negative pressure and has no adverse impact upon the wafer fabrication tool 202. From collection header 208, the gas mixture is passed in feed line 224 to compressor 210.

Compression of the collected gases to about 100–150 psig (about 7.8–10 atmospheres) is accomplished with the compressor 210. In one embodiment of the invention, this compressor may be a liquid ring compressor which operates with a recirculated dilute caustic liquid seal. The liquid ring compressor can be operated with its suction controlled at a slight negative pressure as mentioned above. A description of liquid ring compression can be found in Perry's Chemical Engineers' Handbook. Other compressor types which may also suitably be employed include piston compressors, gear compressors, and rotary vane compressors.

Collection header pressure is suitably monitored by a pressure gauge 226 in pump discharge line 228 which is immediately upstream of back-pressure regulator 230 in discharge line 228. Flow control valve 232 in header recycle line 234 releases gas as required to control the collection header pressure and maintain a selected load level on the compressor 210.

Any acid gases or other by-products (for example, HF, $H_2SiF_6$, $BCl_3$, HCl, $Cl_2$, $SiF_4$) remaining in the collected streams are flowed to collection header 208, absorbed and neutralized by the dilute caustic as seal liquid in the compressor 210.

When compressor 210 comprises a liquid ring pump, dehydration of the caustic neutralized gas is required because water generally interferes with carbon adsorption and selectivity. System operation with dry scrubbers and dry compression equipment may be employed and the actual compression sequence selected on technical and economic grounds. Dehydration of the compressed gas can be accomplished by a heat-less dryer (not shown) which is designed for this process. A two bed heatless dryer can be used which is identical to dryers used for compressed air except that the dryer exhaust is suitably recycled back to the compressor suction of compressor 210 so as to avoid any unnecessary loss of halocarbon gas. For a compressor discharge pressure of 100 psig, the flow of gas for reactivation of the dryer beds will be about 15–20% of the compressor flow.

Halocarbon concentration is accomplished by a pressure swing adsorption process (PSA) carried out in the PSA system 242 comprising adsorbent beds 244 and 246 and cooperatively coupled with each other between a first PSA manifold 247 and a second PSA manifold 248 in a known and conventional manner. Multiple bed PSA systems utilizing two or more beds manifolded together for intermittent or continuous adsorption operation of widely varying types may be used in the broad practice of the present invention. A three-bed cascade adsorption system is described, for example, in Bulkeley, Chem. Met. Eng., 45, 300 (1938) and U.S. Pat. Nos. 4,070,164 ("Adsorption-Desorption Pressure Swing Gas Separation") and 4,645,516 ("Enhanced Gas Separation Process") describe other potentially useful PSA systems. The disclosures of these references hereby are incorporated herein by reference.

The desired product (concentrated halocarbon stream) of the PSA processing is the material retained on the adsorbent. A simple description of the sequence follows.

At system pressure (70–200 psig, preferably 100–120 psig), the halocarbon-containing gas is passed through one of the adsorbent beds 244 and 246, where the halocarbon is adsorbed onto the bed and the gas vented through line 248 and back-pressure regulator 271 and exit line 270. If adsorbent bed 244 is the currently active adsorbing bed, then bed 246 is being regenerated, and actuated valve 280 is open and gas flows in line 282 to the vacuum section 284.

Check valves 272, 273, 274 and 276 direct flow and prevent backflow into the cannister that is being regenerated. When adsorbent bed 244 is serving as the active absorber, valve 278 in conduit line 279 is closed, thereby preventing gas flow to check valve 274 and therefore preventing back-flow to adsorbent bed 246. Check valve 276 prevents back-filling of adsorbent bed 246.

The partly depressurized bed is additionally vented countercurrently back into the compressor suction of compressor 210 via lines 240 and 234, or alternatively, in lines 250, 208 and 224 (depending on which bed is actively adsorbing and which bed is regenerating).

Concentration of the halocarbon occurs during the desorption step when the partial pressure is similar to the adsorption partial pressure, but the system total pressure is substantially lower.

After the bed that is being regenerated, absorber bed 246, is suitably clean, valve 278 is opened and the vent gas from the active absorber 244 is used to back-fill in a counter current fashion the just-regenerated absorber bed 246.

After the pressure in 246 is suitably high, the valves are switched to make it the active adsorbing tank. The tank 244 that was the active adsorbing tank is now regenerated. One bed is always on stream for adsorption.

The vacuum pump section 284 is set up to protect the vacuum pump 286 from high pressures. Until the pressure in line 282 reaches a suitably low level, the gas is routed through line 250 back to the main header line 208. The gas stream contains halocarbons that may be recovered on subsequent passes through the absorber bed(s). Vacuum section 284 is further equipped to increase the concentration of halocarbon by venting more of the dilute halocarbon mixture back into the header line for recovery. When the concentration of halocarbon becomes suitably high, the gases are routed through line 260 to be compressed by compressor pump 262.

Compression of the recovered halocarbon is relatively inexpensive and is carried out by flowing the halocarbon in product line 260 to a three stage compressor system 262. One or more cylinders 264, 266 may be connected to a filling header 268 which operates under automatic control to package the recovered halocarbon for recycle, disposition or other use.

Depending upon the initial concentration of halocarbon and the pressure ratios employed as well as the process design, it may be desirable to repeat the above sequence with the concentrated halocarbon product from the above described sequence. Experimental data as well as the purity and concentration requirements for recycling may readily be used to determine if a second stage of compression and PSA is required.

In the practice of the present invention, the adsorbent for adsorbing the halocarbon is selected on the basis of its capacity for halocarbon. Suitable materials include high surface area adsorbents such as activated carbon, molecular sieves, aluminas, silica gel, and macroreticulate organic polymers such as Amberlite. Activated carbon is preferred. Carbon is an excellent adsorbent for halocarbons; its high polarizability suits it well for adsorption of non-polar molecules such as $C_2F_6$, and related species.

If an activated carbon adsorbent bed(s) is characterized as to its capacity for one of the halocarbon gases, its adsorptive performance may be predicted for many other halocarbon species using data published by Wood and Stampfer (Carbon 31, 195–200, 1993; Carbon 30, 593, 1992) and by Nelson et al. (Am. Ind. Hyg. Assoc. J. 33, 797 (1972); Am. Ind. Hyg. Assoc. J. 52, 235 (1991)).

Figure 3:
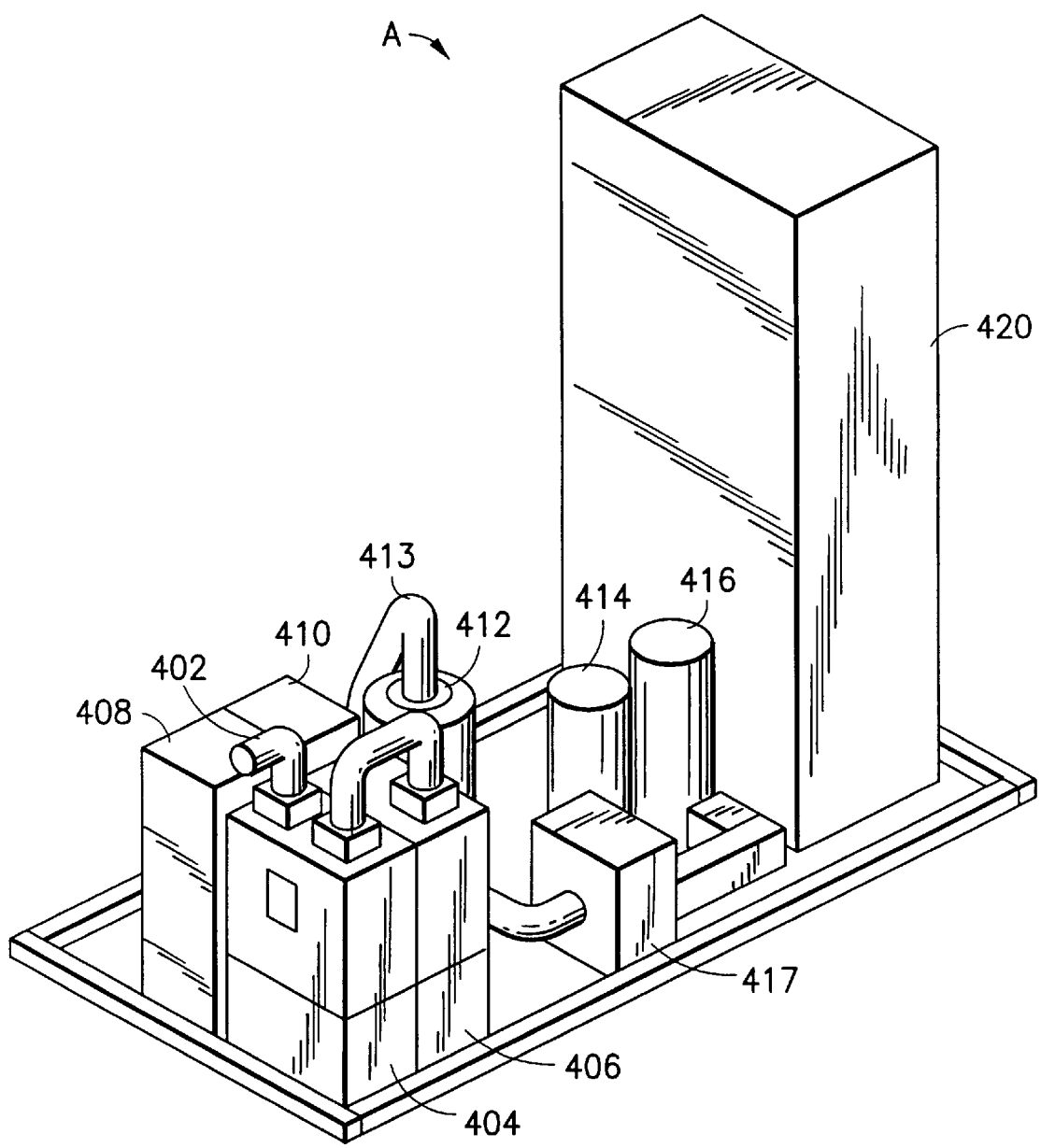
FIG. 3 shows a perspective view of an apparatus for scrubbing, concentration, and recovery steps that comprise one embodiment of the method of the present invention, employing a cryogenic recivery unit.

Referring now to FIG. 3, wherein a particularly preferred embodiment is shown, process exhaust from a fab containing halocarbons and acid gas by-products enters into conduit 402 and passes through wet scrubbers 404 and 406 in series to provide maximum acid gas removal efficiency and to minimize water usage. Water flow is countercurrent beginning at scrubber 406 and flowing forward to scrubber 404. Scrubbers 404 and 406 are of a size such that system A can optionally operate using only one of scrubbers 404 or 406, providing there is system redundancy. For more efficient hydrolysis/neutralization of acid gases, each scrubber 404 and 406 is maintained at a pH of 9 or above using caustic addition modules 408 and 410. Wet scrubbers 404 and 406 are operated at relatively low temperatures to reduce the volume of water vapor added to the exhaust stream. Once acid gases are removed from the process exhaust by scrubbers 404 and 406, the exhaust stream is conveyed to dry scrubber 412 via conduit 413 to remove hydride gas impurities such as silane, arsine and phosphine. At this point the exhaust stream is comprised of carrier gas, some water vapor, halocarbon and small amounts of low reactivity impurities such as CO. Blower 417 is used to convey the exhaust stream through water removal system columns 414 and 416. This dual column arrangement permits one unit to be on line and operating while the second unit is regenerating or in reserve. The effluent from the water removal system becomes a feed stream to cryogenic recovery unit 420. In an alternative embodiment the effluent stream may pass through water removal unit columns 414 and 416 before it passes through dry scrubber 412.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. A process for recovery of fluorocompound gas selected from the group consisting of perfluorocarbons, fluorinated hydrocarbons, chlorofluorocarbons, sulfur hexafluoride, nitrogen trifluoride, and mixtures thereof, from an effluent gas stream comprising said fluorocompound gas and other gas components, said process comprising the steps of:
first removing at least one of said other gas components from the effluent stream to yield a first effluent gas mixture containing said fluorocompound gas; and
removing said fluorocompound gas from the first effluent gas mixture and recovering same as a concentrated fluorocompound gas,
wherein said first removing said at least one gas component, comprises a step selected from the group consisting of:
(i) oxidizing said at least one gas component for removal of same from the effluent gas stream;
(ii) contacting the effluent gas stream with a dry material which is effective for removal of said at least one gas component from the effluent gas stream; and
(iii) combinations of steps (i) and (ii).

2. A process according to claim 1, wherein the first effluent gas mixture contains water, and the first effluent gas mixture is dried to remove water therefrom prior to said removing said fluorocompound gas from the first effluent gas mixture and recovering same as the concentrated fluorocompound gas.

3. A process according to claim 1, wherein removing said fluorocompound gas from the first effluent gas mixture and recovering same as said concentrated fluorocompound gas comprises processing steps selected from the group consisting of:
(a) contacting at least one time and under superatmospheric pressure, the first effluent gas mixture with an adsorbent which is selective for said fluorocarbon gas to adsorb said fluorocompound gas on the adsorbent and yield a second effluent gas substantially free of said fluorocompound gas; and
recovering the adsorbed fluorocompound gas by desorbing same from the adsorbent to recover desorbed fluorocompound gas as said concentrated gas; and
(b) subjecting at least one time, the first effluent gas mixture to a cryogenic recovery system to concentrate and recover said fluorocompound gas as said concentrated fluorocompound gas.

4. A process according to claim 1, wherein the step of removing said fluorocompound gas from the first effluent gas mixture and recovering same as said concentrated fluorocompound gas is carried out in a cryogenic recovery system.

5. A process according to claim 2, wherein said drying comprises contacting the effluent gas stream with a molecular sieve, silica gel or a surface that is maintained at sufficiently low temperature that any water in said first effluent gas mixture will condense out on said surface.

6. A process according to claim 1, wherein said step of removing said at least one gas component of said effluent gas stream comprises contacting the effluent gas stream with a material selected from the group consisting of goethite, copper oxide, copper sulfate, calcium oxide, lithium hydroxide, zinc oxide, a polymeric metal complex, and mixtures thereof.

7. A process according to claim 1, wherein said fluorocompound gas comprises a compound selected from the group consisting of perfluoroethene, perfluoroethane, trifluoromethane, carbon tetrafluoride, sulfur hexafluoride and mixtures thereof.

8. A process according to claim 1, wherein the concentration of fluorocompound gas in said gas mixture does not exceed about 5% by weight, based on the total weight of the effluent gas stream.

9. A process according to claim 1, wherein the recovered fluorocompound gas is compressed and flowed to a gas cylinder.

10. A process according to claim 3, wherein said adsorbent comprises a material selected from the group consisting of molecular sieves, activated carbon, activated alumina, silica, macroreticulate organic polymers, polymeric metal complexes, and mixtures thereof.

11. A process according to claim 1, wherein said step of removing said at least one gas component from said effluent gas stream includes multiple removal steps.

12. A process according to claim 1, wherein removing said fluorocompound gas from the first effluent gas mixture and recovering same as a concentrated fluorocompound gas comprises steps selected from those of the group consisting of:

(A) selectively adsorbing said fluorocompound gas from the first effluent gas mixture on an adsorbent selective therefor to separate the fluorocompound gas from other gas components of the first effluent gas mixture, desorbing the fluorocompound gas from the adsorbent, and recovering desorbed fluorocompound gas as said concentrated fluorocompound gas;

(B) cooling said first effluent gas mixture to liquify or solidify said fluorocompound gas from the first effluent gas mixture, and form a fluorocompound condensate, and recovering said concentrated fluorocompound gas from said fluorocompound condensate; and (C) confining said first effluent gas mixture against a selective membrane allowing passage therethrough of gas components of the first effluent gas mixture other than said fluorocompound gas, to concentrate the fluorocompound gas and discharge the gas components of the first effluent gas mixture other than said fluorocompound gas, and recovering confined fluorocompound gas as said concentrated fluorocompound gas.

13. A process according to claim 1, further comprising flowing the concentrated fluorocompound gas to a gas cylinder for containment therein.

14. A process according to claim 1, wherein said step of removing said fluorocompound gas from said first effluent gas mixture and recovering same as a concentrated fluorocompound gas, comprises cryogenic separation of said fluorocompound gas from the first effluent gas mixture and recovery of same as a concentrated fluorocompound gas.

15. A process for recovery of fluorocompound gas selected from the group consisting of perfluorocarbons, fluorinated hydrocarbons, chlorofluorocarbons, sulfur hexafluoride, nitrogen trifluoride, and mixtures thereof, from an effluent gas stream comprising said fluorocompound gas and other gas components including at least one gas component selected from the group consisting of hydrides, silane, silane/oxygen mixtures, silane/$NF_3$ mixtures, perfluoro compounds, and combinations thereof, said process comprising the steps of:
first removing said at least one gas component therefrom, thereby yielding a first effluent gas mixture containing said fluorocompound gas; and
removing said fluorocompound gas from the first effluent gas mixture and recovering same as a concentrated fluorocompound gas, wherein said first removing said at least one gas component, comprises a step selected from the group consisting of:
(i) oxidizing said at least one gas component for removal of same from the effluent gas stream;
(ii) contacting the effluent gas stream with a dry material reactive with said at least one gas component for removal of said at least one gas component from the effluent gas stream; and
(iii) combinations of steps (i) and (ii).

16. A process for recovery of fluorocompound gas selected from the group consisting of perfluorocarbons, fluorinated hydrocarbons, chlorofluorocarbons, sulfur hexafluoride, nitrogen trifluoride, and mixtures thereof, from an effluent gas stream comprising said fluorocompound gas and other gas components, said process comprising the steps of:

removing at least one of said other gas components therefrom to deplete the effluent gas stream in at least one of said gas components and concentrate said fluorocompound gas in the gas phase therein, thereby yielding a first effluent gas mixture containing said gas phase fluorocompound gas; and removing said gas phase fluorocompound gas from the first effluent gas mixture and recovering same as a concentrated fluorocompound gas, wherein removing said fluorocompound gas from the first effluent gas mixture and recovering same as a concentrated fluorocompound gas is carried out with at least two adsorbent beds, each of said adsorbent beds having inlet and outlet ends, respectively, and joined at inlet and outlet ends thereof to gas feed and gas discharge manifolds, respectively, wherein said first effluent gas mixture is introduced to one of said absorbent beds from said gas feed manifold at superatmospheric pressure to effect adsorption of fluorocompound gas on the bed, and contemporaneously another of said adsorbent beds is depressurized following adsorption of fluorocompound gas thereon, to desorb the adsorbed fluorocompound gas and to discharge same from the bed through said gas discharge manifold at lower-than-first superatmospheric pressure, and wherein such steps are alternatively and repetitively carried out in respective adsorbent beds.

* * * * *

UNITED STATES PATENT AND TRADEMARK OFFICE
CERTIFICATE OF CORRECTION

PATENT NO : 6,030,591
DATED : Feb. 29, 2000
INVENTOR(S) : Glenn M. Tom; H. Eric Fisher; Karl Olander It is certified that error appears in the above-identified patent and that said Letters Patent are hereby corrected as shown below:

Column 5, line 5:      replace "inter alia" with --*inter alia*--.
Column 5, line 29:     change "thernmal" to --thermal--.
Column 6, line 21:     change "hexafluorodisilanc" to --hexafluorodisilane--.
Column 6, line 52:     after "thereof" insert --.--.
Column 9, line 62:     change "Chem. Met. Eng." to --*Chem. Met. Eng.*--.
Figure 1 should be labeled according to the application.

Signed and Sealed this

Third Day of April, 2001

*Attest:*

NICHOLAS P. GODICI

*Attesting Officer*  *Acting Director of the United States Patent and Trademark Office*